US00PP33227P3

(12) United States Plant Patent
Larse

(10) Patent No.: US PP33,227 P3
(45) Date of Patent: Jul. 6, 2021

(54) STRAWBERRY PLANT NAMED 'PERSEPHENE'

(50) Latin Name: ***Fragaria* x *ananassa***
Varietal Denomination: Persephene

(71) Applicant: Sweet Darling Sales, Inc., Aptos, CA (US)

(72) Inventor: John Larse, Watsonville, CA (US)

(73) Assignee: Sweet Darling Sales, Inc., Aptos, CA (US)

( * ) Notice: Subject to any disclaimer, the term of this patent is extended or adjusted under 35 U.S.C. 154(b) by 0 days.

(21) Appl. No.: 16/873,475

(22) Filed: Apr. 17, 2020

(65) Prior Publication Data

US 2020/0337192 P1 Oct. 22, 2020

Related U.S. Application Data

(60) Provisional application No. 62/835,705, filed on Apr. 18, 2019.

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./156, 208
See application file for complete search history.

(56) References Cited

U.S. PATENT DOCUMENTS

| | | | |
|---|---|---|---|
| PP7,614 | P | 8/1991 | Bringhurst et al. |
| 2020/0337191 | P1 | 10/2020 | Larse |
| 2020/0337193 | P1 | 10/2020 | Larse |

*Primary Examiner* — Susan McCormick Ewoldt
*Assistant Examiner* — Karen M Redden
(74) *Attorney, Agent, or Firm* — Cooley LLP

(57) ABSTRACT

The present invention provides a new and distinct strawberry variety designated as 'Persephene' (a.k.a. '110195'). The 'Persephene' cultivar is primarily adapted to growing conditions of the central coast of California and produces strong vigorous plants that remain in fruit production from March through October.

7 Drawing Sheets

Latin name of the genus and species: *Fragaria* x *ananassa.*

Varietal denomination: 'Persephene'.

BACKGROUND OF THE INVENTION

The present invention relates to a new and distinct strawberry variety designated as 'Persephene' (a.k.a. '110195').

'Persephene' (a.k.a. '110195') is the result of a controlled-cross between a female parent cultivar designated '108080' and a male parent cultivar designated '107801', and was first fruited in Watsonville, Calif. growing fields. Both parents are proprietary strawberry plant varieties made by the inventor and are not available to the public. Following selection and during testing, the plant was originally designated '110195' and subsequently named 'Persephene'.

This new variety was asexually reproduced via runners (stolons) by the inventor at Watsonville, Calif. Asexual propagules from the original source have been tested in Watsonville growing fields and to a limited extent, grower fields in high elevation. The properties of this variety were found to be transmissible by such asexual reproduction. This cultivar is stable and reproduce true to type in successive generations of asexual reproduction.

DESCRIPTION OF THE DRAWINGS

The accompanying color photographs depict various characteristics of the cultivar as nearly true as possible to make color reproductions. The age of the plants in FIGS. 1-7 is six months old.

SUMMARY OF THE INVENTION

Figure 1:
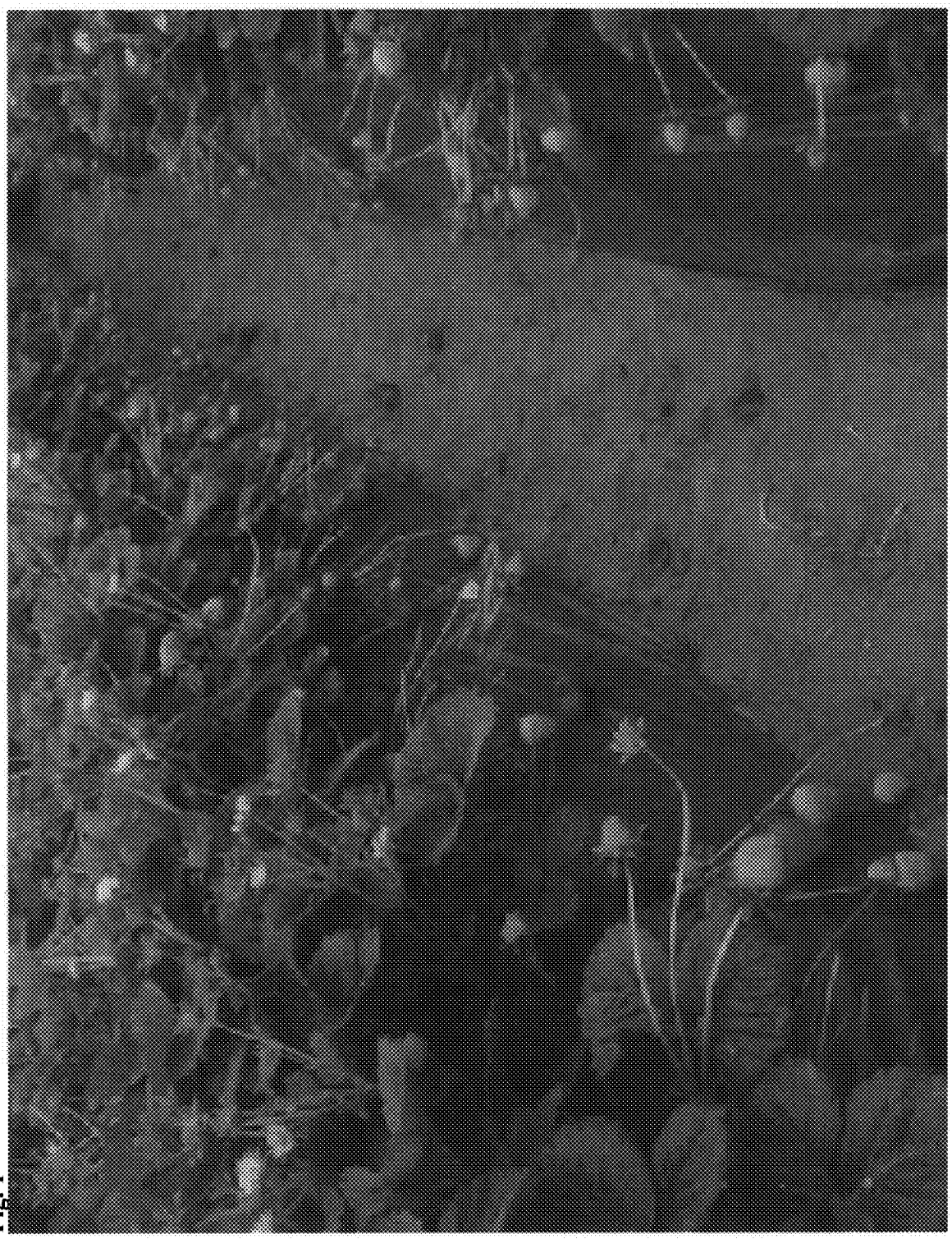
FIG. 1 shows 'Persephene' plant with florescence and fruit.
Figure 2:
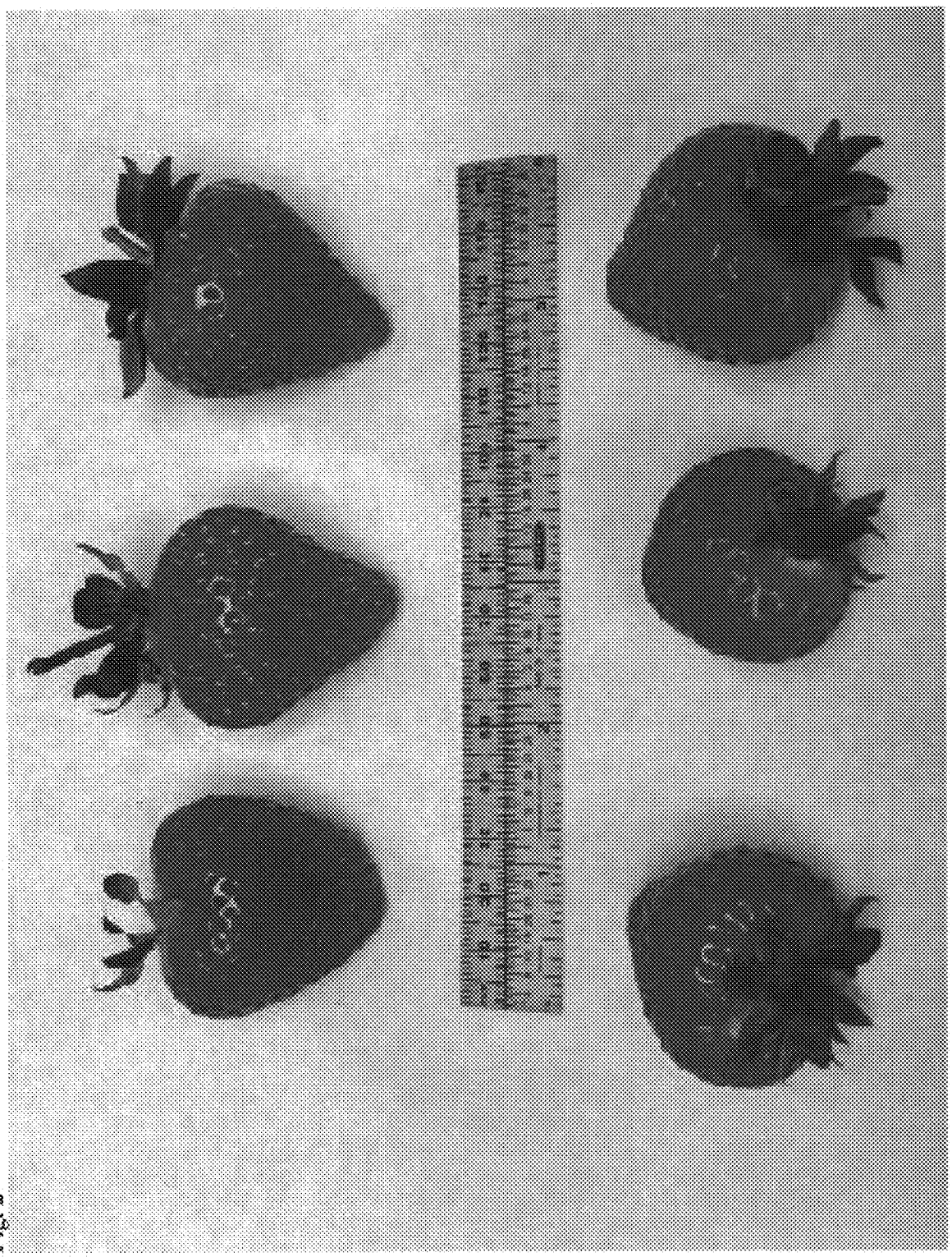
FIG. 2 shows 'Persephene' fruit.
Figure 3:
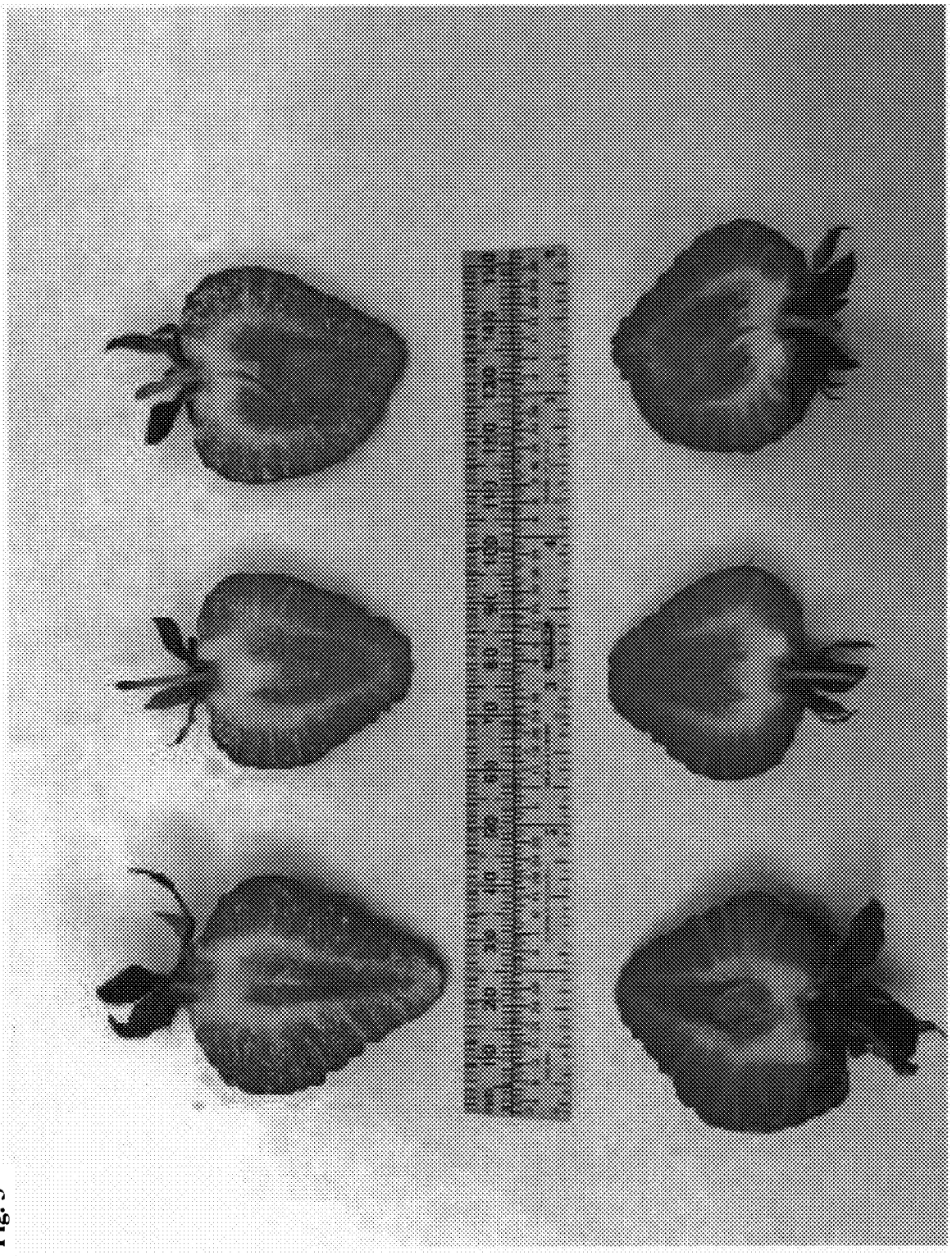
FIG. 3 shows 'Persephene' fruit cross section.
Figure 4:
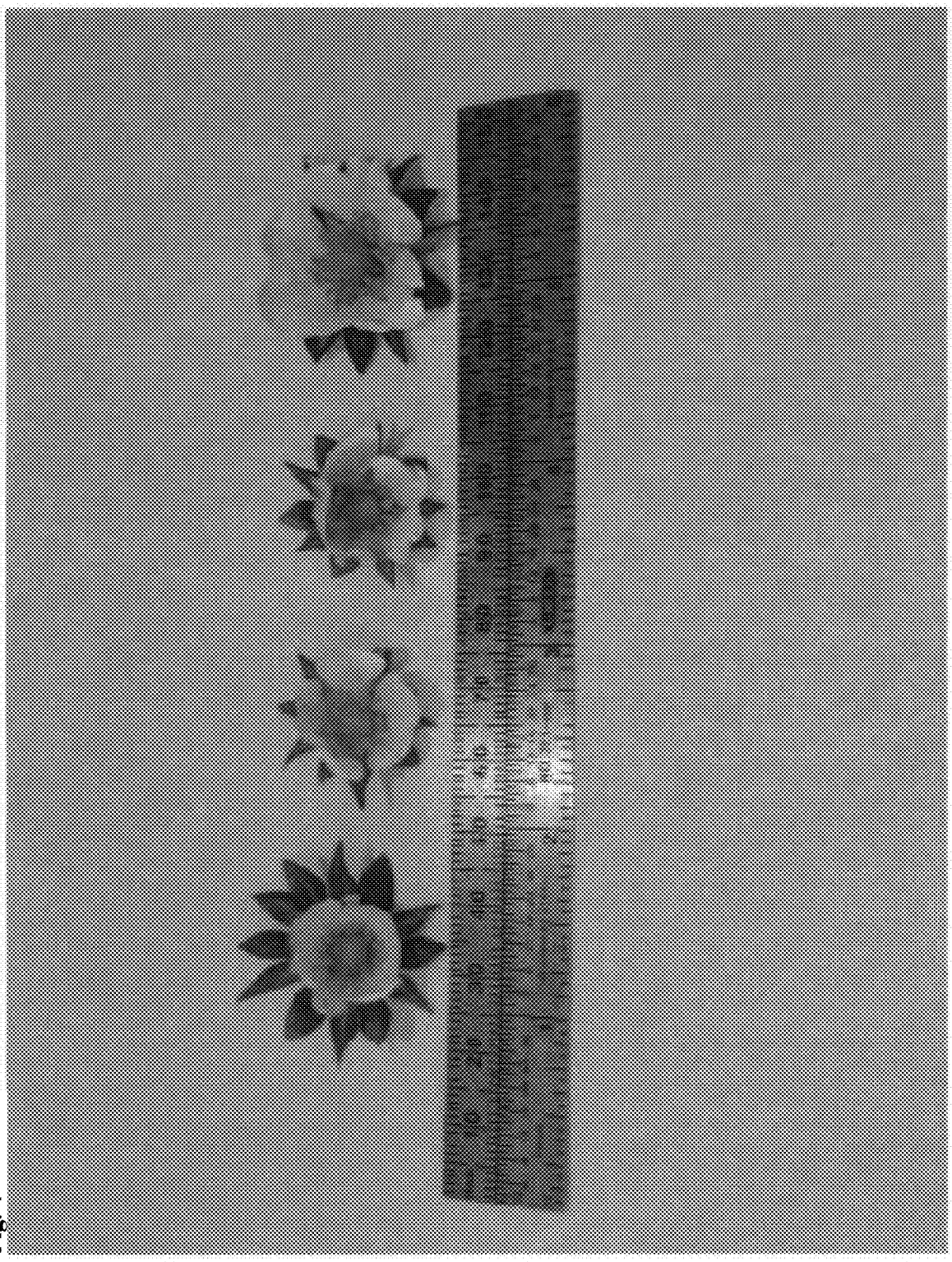
FIG. 4 shows 'Persephene' flowers.
Figure 5:
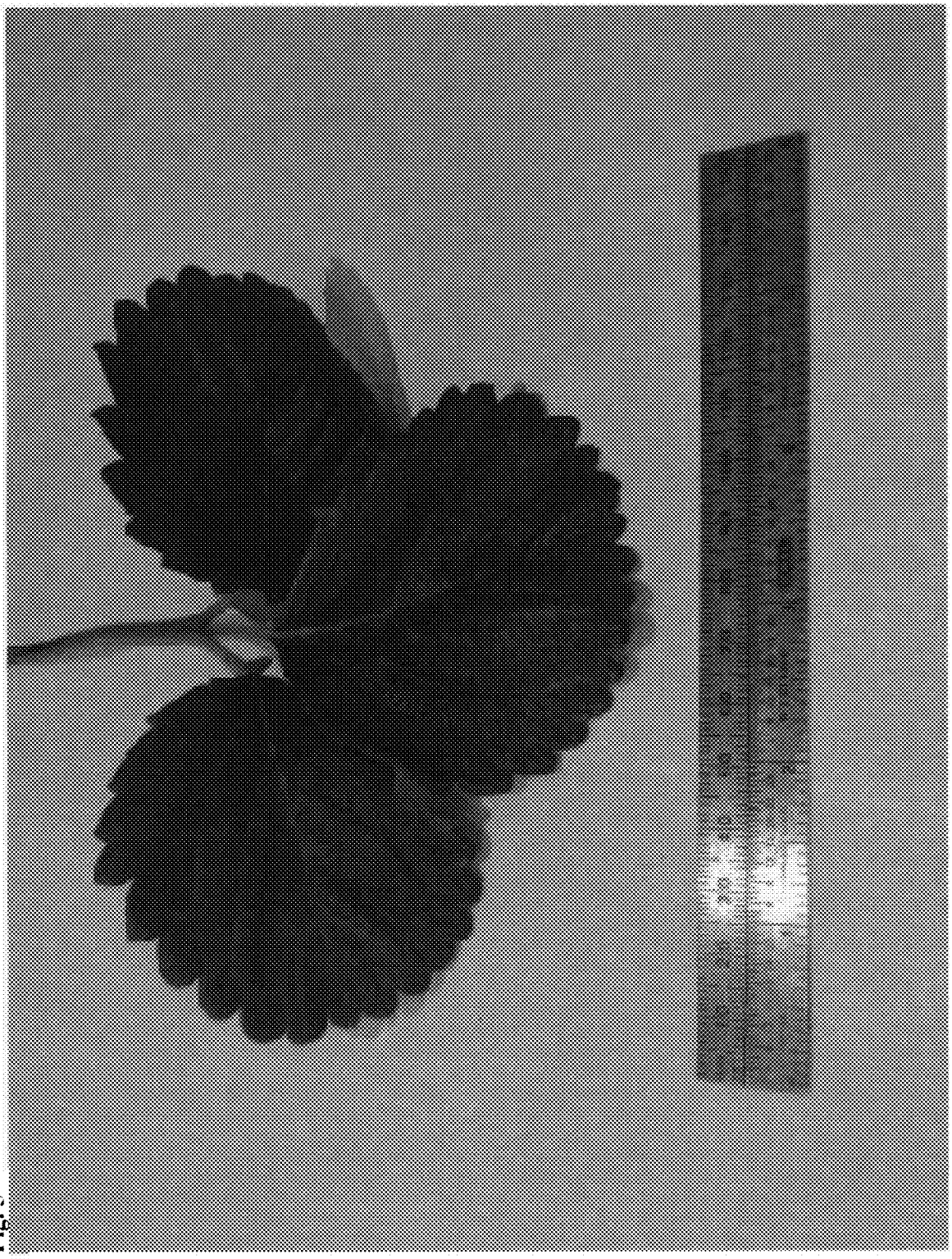
FIG. 5 shows 'Persephene' leaf.
Figure 6:
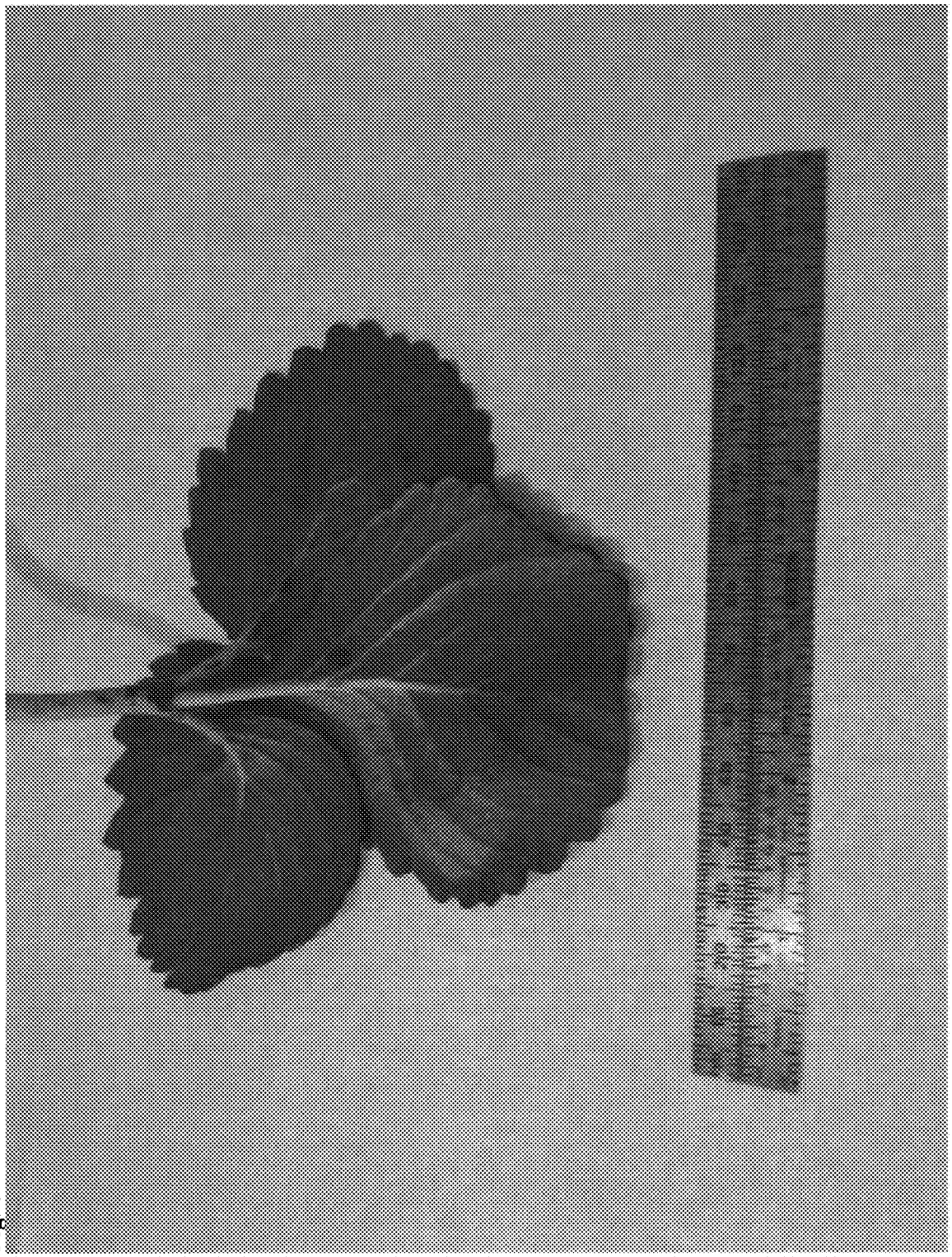
FIG. 6 shows 'Persephene' underside leaf.
Figure 7:
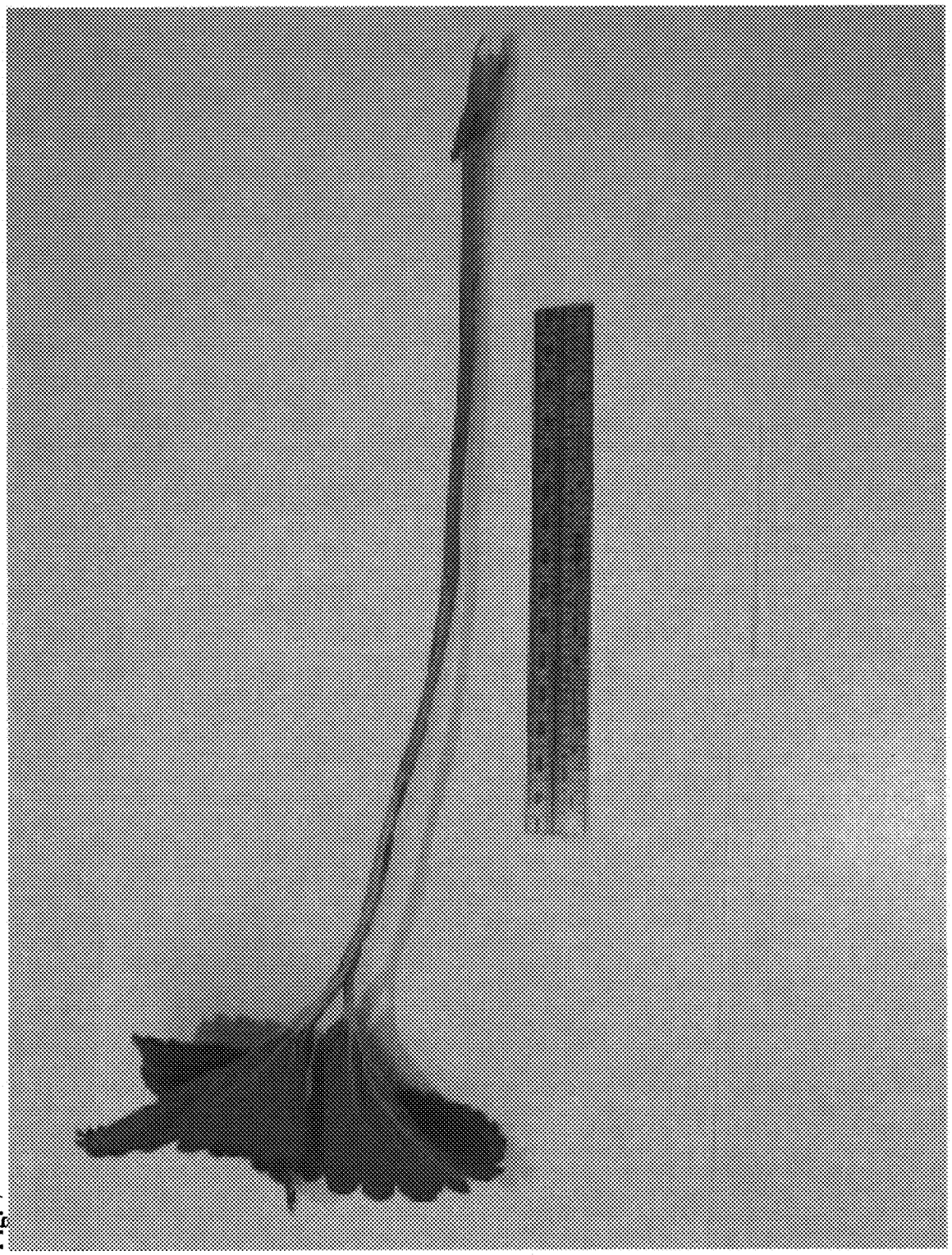
FIG. 7 shows 'Persephene' petiole.

This invention relates to a new and distinctive strawberry cultivar designated as 'Persephene' (a.k.a. '110195'). This cultivar is primarily adapted to the climate and growing conditions of the central coast of California. This region provides the necessary temperatures required for it to produce a strong vigorous plant and to remain in fruit production from March through October. The nearby Pacific Ocean provides the needed humidity and moderate day temperatures and evening chilling to maintain fruit quality for the production months.

The following traits and photographs in combination distinguish the strawberry variety 'Persephene' from known strawberry varieties. Plants for the botanical measurements in the present application were grown as annuals. Any color references are made to The Royal Horticultural Society Colour Chart, 1995 Edition, except where general terms of ordinary dictionary significance are used. The age of the plants in Table 1 is seven months old.

TABLE 1

| Characteristics of Persephene | | |
|---|---|---|
| Characteristic Type | Characteristic | Persephene |
| General | Plant Habit | annual |
| | Plant Growth Habit | semi-upright to spreading |
| | Day length | neutral |
| | Planting season | Fall |
| | Height | 41 cm |
| | Width | 47 cm |
| | Density of foliage | light to medium |
| | Plant vigor | high |
| | Freezing Quality | moderate |
| | Rain/weather tolerance | moderate |
| | Harvest Ease | easy |
| Leaf | Leaf Shape | concave |
| | Leaf texture | soft |
| | Leaf average width | 138 mm |
| | Leaf average length | 114 mm |
| | Terminal leaflet width | 79 mm |
| | Terminal leaflet length | 76 mm |
| | Terminal leaflet length/width ratio | 0.96 |
| | Teeth per terminal leaflet | 16 to 22 |
| | Shape of the terminal leaflet base | acute to rounded |
| | Shape of terminal leaflet in cross-section | concave |
| | Shape of the terminal leaflet margin | serrate to crenate |
| | Color of upper side of leaflet | RHS 137A |
| | Color of lower side of leaflet | RHS 138B |
| | Leaf blistering | weak |
| | Leaf glossiness | weak to medium |
| | Leaf variegation | absent |
| | Number of leaflets per leaf | 3 |
| | Terminal Leaflet margin | revolute |
| | Terminal Leaflet shape | orbicular |
| | Terminal Leaflet shape of apex | rounded |
| Limbs | Petiole length | 29 cm |
| | Petiole diameter | 3.86 mm |
| | Petiole pubescence | sparse to medium |
| | Petiole pose of hairs | upwards |
| | Petiole color | RHS 145A |
| | Petiolule length | 1.3 to 6.0 cm |
| | Petiolule diameter | 2.86 mm |
| | Petiolule color | RHS 145A |
| | Stipule length | 4.5 cm |
| | Stipule width | 1.2 cm |
| | Stipule pubescence | medium |
| | Stipule anthocyanin | present |
| | Stipule color (color code) | RHS 145C |
| | Pedicel average length | 19.4 cm |
| | Pedicel average diameter | 2.7 mm |
| | Pedicel color (color code) | RHS 145A |
| | Attitude of hairs on peduncle and pedicel | upwards |
| | Peduncle average length | 125 mm |
| | Peduncle average diameter | 4.5 mm |
| Inflorescence | Inflorescence position relative to foliage | above |
| | Flower arrangement of petals | free to touching |
| | Flower size | medium |
| | Flower diameter | 2.8 cm |
| | Petal shape | orbicular |
| | Petal apex | rounded |
| | Petal margin | entire |
| | Petal base shape | concave |
| | Petal length | 1.1 to 1.3 cm |
| | Petal width | 1.1 to 1.2 cm |
| | Petal length/width ratio | 1 to 1.08 |
| | Petal number per flower | 5 |
| | Number of flowers | 36 to 40 |
| | Upper Petal color | RHS 155D |
| | Lower Petal color | RHS 155D |
| | Floral Calyx Diameter | 41 cm |
| | Corolla diameter | 28 cm |
| | Calyx diameter relative to corolla | larger |

TABLE 1-continued

| Characteristics of Persephene | | |
|---|---|---|
| Characteristic Type | Characteristic | Persephene |
| | Inner calyx diameter relative to outer calyx | same size |
| | Sepal shape | elliptical |
| | Sepal apex | convex |
| | Sepal margin | entire |
| | Sepal length | 1.1 cm |
| | Sepal width | 0.4 to 0.7 cm |
| | Sepal number per flower | 12 |
| | Sepal color (upper) | 137A |
| | Sepal color (lower) | 138B |
| | Receptacle color | RHS 141D |
| | Fertility | not tested |
| | Time of flowering (50% of plants in bloom) | May |
| | Shape of stigma | capitate |
| | Color of stigma | 163B |
| | Length of style | 1.4 mm |
| | Color of style | RHS 4A |
| | Color of the ovary | RHS 150B |
| | Number of stamen | 18 to 24 |
| | Length of the stamens | 1.5 to 5.0 mm |
| | Shape of anther | dorsifixed |
| | Size of anther | 1.5 mm |
| | Color of anther | RHS 20A |
| | Amount of pollen | scarce |
| | Color of pollen | RHS 21B |
| | Color of filament | RHS 150B |
| | Length of filament | 0.5 to 3.5 mm |
| Stolon | Stolon number | 1 to 4 |
| | Stolon anthocyanin | RHS 166A |
| | Stolon thickness | medium |
| | Stolon pubescence | sparse |
| | Widest diameter of stolon at leaf attachment | 2.71 mm |
| | Stolon average length | 50.6 cm |
| | Stolon color | RHS 145A |
| Fruit | Fruiting truss length | 6.5 to 24.0 cm |
| | Fruiting truss diameter | 3.03 mm |
| | Number of fruit per truss | 3 to 7 |
| | Truss color | RHS 145A |
| | Fruit length | 3.7 to 4.3 cm |
| | Fruit width | 3.7 to 3.9 cm |
| | Fruit skin color | RHS 45A |
| | Fruit flesh color excluding core | RHS 41A |
| | Fruit core color | RHS 38A |
| | Fruit length/width ratio | 1.0 to 1.11 |
| | Fruit weight | June: 26.7 g |
| | Relative fruit size | medium to small |
| | Predominant fruit shape | conic to globose conic |
| | Shape difference between primary & second | No shape difference |
| | Width of band without of achenes | medium to narrow |
| | Fruit glossiness | medium |
| | Position of achenes | below surface |
| | Achene color | RHS 185B |
| | Achenes per fruit | 405 |
| | Achene weight | 0.238 g |
| | Position of calyx | below surface |
| | Fruit Calyx Diameter | 4.1 cm |
| | level of adherence of calyx | weak |
| | Color of calyx | RHS 137C |
| | Pose of calyx segments | reflexed |
| | Size of calyx in relation to fruit | larger |
| | Firmness of flesh | medium |
| | Evenness of flesh color | nearly even |
| | Fruit hollow length | 1.8 cm |
| | Fruit hollow width | 1.2 cm |
| | Fruit hollow length/width ratio | 1.5 |
| | Hollow center | small |
| | Sweetness | 7 to 7.5 Brix |
| | Acidity | 3.54 |

TABLE 1-continued

| Characteristics of Persephene | | |
|---|---|---|
| Characteristic Type | Characteristic | Persephene |
| | Texture when tasted | medium |
| | Time of flowering | May |
| | Time of fruit ripening | June |
| | Harvest maturity (50% of plants with ripe fruit) | June |
| | Type of bearing | day neutral |
| | Grams of fruit per plant (weeks 17 to 37) | 1468 g |
| | Yield (lb per acre) | June: 30,000 lb/acre |
| | Firmness | firm |
| | Surface Texture | smooth |
| | Fruit Appearance (1-7 scale; 7 = best) | 6 |
| | Storage longevity | 10 days |
| | Mean percent marketable fruit (weeks 17 to 37) | 86% |
| Horticultural | Crop suitability | Fresh market |
| | Temperature tolerance range | −1° C. to 36° C. |
| | USDA Hardiness Zone adaptability for annual transplanting of California grown commercial rootstock | 6a,6b,7a,7b, 8a,8b,9a,9b |
| | Cull rate (% Usable) | 12% |

'Seascape' (U.S. Plant Pat. No. 7,614) is a commercial strawberry variety that is similar to, but distinguished from 'Persephene'. The foliage of the new strawberry plant variety 'Persephene' was observed to be more dense than the foliage of the check variety 'Seascape'. The florescence of the new variety 'Persephene' pollinates beyond the canopy and differs in this way from 'Seascape'. Some of the flowers of the comparison strawberry variety 'Seascape' do not extend beyond the leaf canopy and some of the fruit of 'Seascape' ripens beneath the canopy. The new variety 'Persephene' is easier to harvest than the check variety 'Seascape'. The fruit color of check variety 'Seascape' is deeper red than the fruit color of new variety 'Persephene'. The yield and percent of marketable fruit of 'Persephene' is greater the yield and percent marketable fruit of 'Seascape'.

The strawberry plant 'Persephene' is differs from each of its parents. The fruit of new variety 'Persephene' is conic shaped, however, the fruit of both of the parents of 'Persephene' are long-conic with the ratio of fruit height to fruit width greater than that of 'Persephene'. The fruit of 'Persephene' is firmer than the fruit of its female parent '107801'. The fruit yield of 'Persephene' is similar to the fruit yield of female parent '107801', however, the fruit yield of 'Persephene' is greater than the fruit yield of male parent '108080' and the percent of marketable fruit produced by 'Persephene' is greater than that of both female parent '107801' and male parent '108080'. The fruit of 'Persephene' is larger than the fruit of male parent '108080'. The strawberry plant 'Persephene' is larger than its male parent '108080'.

The invention claimed is:

1. A new and distinct cultivar of strawberry plant named 'Persephene' substantially as shown and described herein.

* * * * *